US009921190B2

United States Patent
Beaty (10) Patent No.: US 9,921,190 B2
(45) Date of Patent: Mar. 20, 2018

(54) METHOD AND APPARATUS TO MONITOR ACOUSTIC PROBES DURING REPAIR

(71) Applicant: General Electric Company, Schenectady, NY (US)

(72) Inventor: Gregory Alan Beaty, Golden, CO (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 186 days.

(21) Appl. No.: 14/866,165

(22) Filed: Sep. 25, 2015

(65) Prior Publication Data

US 2017/0089868 A1    Mar. 30, 2017

(51) Int. Cl.
    *G01N 29/30*    (2006.01)

(52) U.S. Cl.
    CPC ....... *G01N 29/30* (2013.01); *G01N 2291/106* (2013.01)

(58) Field of Classification Search
    CPC .................. G01N 29/30; G01N 2291/106
    USPC ........................................................ 73/1.82
    See application file for complete search history.

(56) References Cited

U.S. PATENT DOCUMENTS

| | | |
|---|---|---|
| 6,920,776 B2 | 7/2005 | Gessert et al. |
| 6,928,856 B2 | 8/2005 | Gessert et al. |
| 7,007,539 B2 | 3/2006 | Gessert et al. |
| 7,028,529 B2 | 4/2006 | Gessert et al. |
| 7,155,957 B2 | 1/2007 | Gessert et al. |
| 7,278,289 B2 | 10/2007 | Gessert et al. |
| D565,444 S | 4/2008 | Moore et al. |
| D599,232 S | 9/2009 | Dananay et al. |
| 7,726,172 B2 | 6/2010 | Moore et al. |
| 7,880,488 B2 | 2/2011 | Dananay et al. |
| 8,008,906 B2 | 8/2011 | Valenti, III |
| 8,159,900 B2 | 4/2012 | Moore et al. |
| 8,164,976 B2 | 4/2012 | Moore et al. |
| 8,169,853 B2 | 5/2012 | Moore et al. |
| 8,199,920 B2 | 6/2012 | Valenti, III |
| D662,843 S | 7/2012 | Ginther et al. |
| 8,714,818 B2 | 5/2014 | Tesic et al. |
| 8,803,532 B2 | 8/2014 | Ginther et al. |
| 8,896,439 B2 | 11/2014 | Mercer et al. |

(Continued)

OTHER PUBLICATIONS

Moore et al., "Testing Device for Acoustic Probes and Systems", U.S. Appl. No. 60/765,273, filed Feb. 2, 2006, 17 pages.

*Primary Examiner* — Helen Kwok
*Assistant Examiner* — Nashimiya Fayyaz
(74) *Attorney, Agent, or Firm* — Hanley, Flight and Zimmerman, LLC (57) ABSTRACT

Methods and apparatus for providing real time measurement of capacitance for a plurality of transducing elements in an acoustic probe during repair are disclosed. An example method includes determining, at a second time, a capacitance of a transducing element of the plurality of transducing elements; when the capacitance of the transducing element is (A) outside an acceptable range and (B) different than an initial capacitance of the transducing element, triggering an alert, the initial capacitance determined at a first time prior to the second time and continuing to determine the capacitance of the transducing element; and when the capacitance of the transducing element is within the acceptable range, continuing to determine the capacitance of the transducing element.

24 Claims, 7 Drawing Sheets

(56) References Cited

U.S. PATENT DOCUMENTS

2005/0245824 A1 11/2005 Schafer et al.
2008/0081958 A1* 4/2008 Denison .............. A61N 1/3706
600/300

* cited by examiner

METHOD AND APPARATUS TO MONITOR ACOUSTIC PROBES DURING REPAIR

FIELD OF THE DISCLOSURE

This disclosure relates generally to acoustic probes and systems and, more particularly, to methods and apparatus for monitoring acoustic probes and systems during repair.

BACKGROUND

Acoustic probes have been found to be extremely valuable in a variety of applications. While medical applications in the form of ultrasound imaging are perhaps the most well-known, acoustic probes are more generally used at a variety of different acoustic frequencies for imaging a variety of different phenomena. For example, acoustic probes may be used for the identification of structural defects, for detection of impurities, as well as for the detection of tissue abnormalities in living bodies. Acoustic probes rely generally on the fact that different structures (e.g., cancerous lesions in a body, defects in an airplane wing, etc.) have different acoustic impedances. When acoustic radiation from an acoustic probe is incident on an acoustic interface, such as where the acoustic impedance changes discontinuously, it may be scattered in ways that permit characterization of the interface. Radiation reflected by the interface is most commonly detected in such applications, but transmitted radiation is also used for such analysis in some applications.

Transmission of the acoustic radiation towards a target and receipt of the scattered radiation may be performed and/or coordinated with a modern acoustic imaging system. Many modern such systems are based on multiple-element array transducers that may have linear, curved-linear, phased-array, or similar characteristics. These transducers may, for example, form part of an acoustic probe. In some instances, the imaging systems are equipped with internal self-diagnostic capabilities that allow limited verification of system operation, but do not generally provide effective diagnosis of the transmission and receiving elements themselves. Degradation in performance of these elements is often subtle and occurs as a result of extended transducer use and/or through user abuse. Acoustic imaging devices therefore often lack any direct quantitative method for evaluating either system or probe performance. Users and technical support personnel thus sometimes use phantoms that mimic characteristics of the object under study to provide a qualitative method for evaluating image quality and to perform a differential diagnosis between the system and the transducer array, but this technique is widely recognized to be of limited utility.

There is, therefore, a general need in the art for apparatus and methods for testing acoustic probes and systems.

SUMMARY

Examples disclosed herein provide real time measurement of capacitance for a plurality of transducing elements in an acoustic probe during repair. An example method disclosed herein includes determining, at a second time, a capacitance of a transducing element of the plurality of transducing elements. In such examples, when the capacitance of the transducing element is (A) outside an acceptable range and (B) different than an initial capacitance of the transducing element, triggering an alert, the initial capacitance determined at a first time prior to the second time and continuing to determine the capacitance of the transducing element. In such examples, when the capacitance of the transducing element is within the acceptable range, continuing to determine the capacitance of the transducing element.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe example implementations and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Examples disclosed herein provide apparatus and methods for testing acoustic probes and systems. Such acoustic probes and systems are sometimes referred to herein collectively as "acoustic devices." While much of the discussion below specifically discusses apparatus and methods that are suitable for testing ultrasonic probes and systems, this is intended merely for exemplary purposes and the invention is not intended to be limited by the operational frequency characteristics used by the tested probe or system. As illustrated in further detail below, each of the acoustic probes and systems that may be tested with embodiments of the invention include a plurality of "transducing elements," which refer to elements adapted to transmit acoustic radiation and/or to receive acoustic radiation. Methods of certain embodiments of the invention diagnose operation of the probe or system in real-time during repair through sequential activation of each of the transducing elements.

For example, testing of an acoustic probe may be performed by connecting electrical leads (e.g., connection pads) of the acoustic probe to electrical leads (e.g., mating connection pads) on a printed circuit board of a monitoring (e.g., testing) device. The printed circuit board connection may be a flexible printed circuit board connection, for example. During initialization (e.g., when the testing device is first activated), each transducing element in the array of transducing elements in the probe is then activated by the monitoring device to measure an initial capacitance for each transducing element. The initial capacitance of each transducing element may be stored and/or displayed to a technician (e.g., user) to inform the technician of the status of the transducing elements (e.g., which transducing elements are functional and/or damaged and how they were damaged (e.g., due to a short, due to a break, a degree of damage, etc.)). After initialization, the technician may repair the acoustic probe while the monitoring device continues to monitor the capacitance of each transducing element in real time. In some examples, the monitoring device determines whether the transducing elements have been fixed or damaged based on whether each transducing element is within a range of acceptable capacitances. The acceptable range is representative of a range of capacitance values associated with an operational transducing element. In some examples, the monitoring device may determine whether the transducing elements have been fixed or damaged based on a comparison of the capacitance of the transducing elements to a threshold value (e.g., a minimum threshold, a maximum threshold, an average threshold) associated with the transducing element. By continuously monitoring transducing element capacitance, if the technician damages a transducing element during repair, the capacitance of the respective transducing element will change to a capacitance outside the acceptable range, and the technician is immediately alerted (e.g., through a visual and/or audible alert) to the damage and/or how the damaged was caused. In some examples, the monitoring device may alert the technician when a transducing element has been repaired (e.g., if the initial capacitance was outside the acceptable range and during repair the capacitance is now within the acceptable range).

An example apparatus and associated method disclosed herein includes determining, at a second time, a capacitance of a transducing element of the plurality of transducing elements. In such examples, when the measured capacitance of the transducing element is (A) outside an acceptable range and (B) different than an initial capacitance of the transducing element, the initial capacitance determined at a first time prior to the second time. In such examples, when the capacitance of the transducing element is within the acceptable range, continuing to determine the capacitance of the transducing element.

Figure 1:
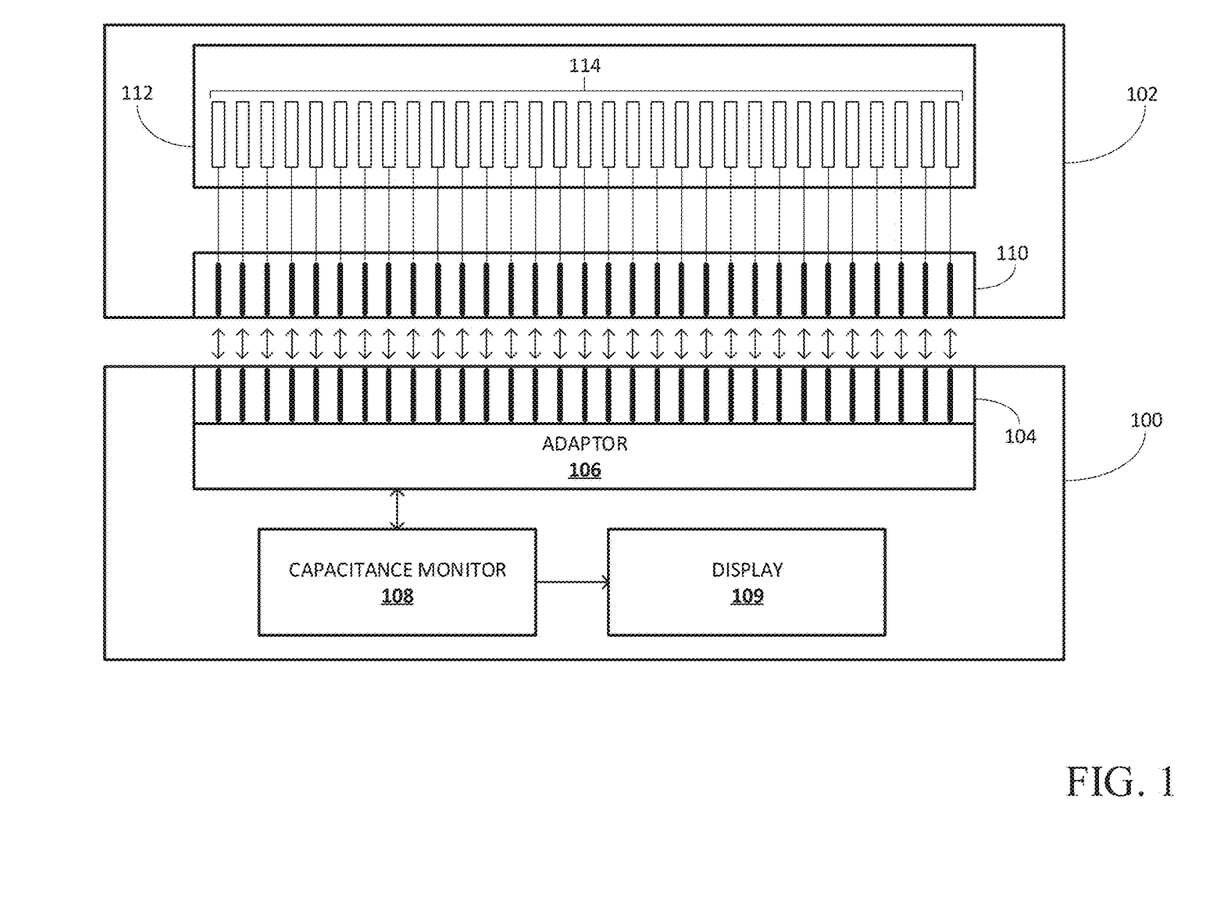
FIG. 1 is an example acoustic probe coupled to an example testing device.

FIG. 1 is an example block diagram of a monitoring device 100 for testing and/or monitoring multiple signals from an acoustic probe 102. The monitoring device 100 includes mating connection pads 104, an adapter 106, a capacitance monitor 108, and a display 109. The acoustic probe 102 includes a plurality of connection pads 110, a transducer 112, and a plurality of transducing elements 114. The monitoring device 100 monitors and/or tests the capacitance of each of the transducing elements 114 in the transducer 112 to trigger an alert (e.g., in real-time or substantially in real-time given a processing and/or transmission delay) that a transducing element 114 from the transducer 112 has been damaged and/or fixed.

The adaptor 106 of the example monitoring device includes the plurality of mating connection pads 104 (e.g., made from conductive material) that may be configured to attach to the plurality of connection pads 110 of the probe 102 to monitor the capacitance of the transducing elements 114. In some examples, the mating connection pads 104 are electric connector pins (e.g., zero insertion force (ZIF) connector pins). In some examples, the adaptor 106 has a mating connection pad 104 for each of the plurality of connection pads 104 as well as power connections, ground connections, computer connections, etc. In some examples, the adapter 106 is configured to provide different schemes for mapping channels from the capacitance monitor 108 to measure capacitance from the acoustic probe 102, as further described in FIGS. 4A and 4B. In some examples, the adapter 106 can be interchangeable with other adapters 106 (e.g., with a different number of mating connection pads 104) configured according to a particular brand model, etc., of an acoustic probe 102.

The capacitance monitor 108 may include any processing device capable of sending instructions to the adaptor 106 to measure capacitances of the transducing elements 114 in the transducer 112, analyzing signals received from the transducer 112, and/or alerting a user and/or another system to discrepancies based on the received signals. For example, the capacitance monitor 108 may include a personal computer, a mainframe, a laptop, a processor, a microcontroller, etc. The capacitance monitor 108 may be implemented using hardware, software, firmware, and/or any combination thereof. Further functionality of the capacitance monitor 108 is described with respect to FIG. 2. If the capacitance monitor 108 triggers an alert, the alert is output via the display 109, for example. The display 109 may be structured to output a visual alert (e.g., a monitor, a light, etc.), an audio alert (e.g., a speaker), and/or a mechanical alert (e.g., a buzzer).

The example acoustic probe 102 includes the connection pads 110, the transducer 112, and the transducing elements 114. In the illustrated example of FIG. 1, the example acoustic probe 102 is an ultrasound probe. Alternatively, the acoustic probe 102 may be a device capable of transmitting acoustic radiation toward a target, and receipt of the scattered radiation may be performed and/or coordinated with an acoustic imaging system and/or other device containing a transducer 112 and/or transducing elements 114. The connection pads 110 are conductive pads structured to connect, at a first end, with the connection mating pads 104 from the monitoring device 100. A second end of the connection pads 110 connects to the transducing elements 114 of the transducer 112. In the illustrated example of FIG. 1, the transducer 112 is a device that can convert acoustic energy to electric energy and vice versa. Alternatively, the transducer 112 can convert a first form of energy (e.g., electrical, mechanical, electromagnetic, chemical, acoustic, thermal, etc.) to another form of energy. In some examples, the transducing elements 114 are piezoelectric crystals that convert vibrations to and/or from electrical signals. Alternatively, the transducing elements 114 may be sensors, probes, microphones, transponders, transceivers, diodes, thermocouples, antennas, fuel cells, thermistors, and/or any other device capable of converting energy from one form to another. Each of the transducing elements 114 has a capacitance value. In some examples, the capacitance values for the transducing elements 114 may change over time. Alternatively or additionally, the capacitance values for the transducing elements 114 and/or hardware associated with the transducing elements 114 may change if they are damaged and/or otherwise rendered inoperable.

In operation, the monitoring device 100 is mounted to the acoustic probe 102 to connect the connection pads 110 of the acoustic probe 102 to the mating connection pads 104 of the monitoring device 100 (e.g., bring the connection pads 110 into physical or proximate contact with the mating connection pads 104). The monitoring device 100 may be mounted to the acoustic probe 102 to allow for real-time (or substantially real-time given a processing and/or transmission delay) monitoring of the acoustic probe 102 during testing, repair, and/or refurbishment of the probe 102. The monitoring device 100 is structured so that the transducing elements 114 of the transducer may be monitored while a technician works on the acoustic probe 102.

Once the monitoring device 100 is mounted, the capacitance monitor 108 determines an initial capacitance measurement (e.g., initialization). During initialization, the capacitance monitor 108 measures a capacitance for each of the plurality of transducing elements 114. In some examples, the capacitance is first discharged from the transducing elements 114 to eliminate an inaccurate reading. The capacitance monitor 108 sends a signal through the adapter 106 to a transducing element 114 in the transducer 112. The adaptor 106 routes the signal through a mating connection pad 110 associated with the transducing element 114. In some examples, the capacitance monitor 108 may determine the capacitance of the transducing element 114 based on a duration of time taken for the transducing element 114 to fully charge, as further described with respect to FIG. 2. Alternatively, the capacitance monitor 108 may use another method of measuring capacitance to determine the capacitance of the transducing element 114. Once the capacitance for the first transducing element 114 is determined, a value associated with the capacitance is stored, and the capacitance monitor 108 measures a capacitance for a second transducing element 114 by sending a second signal to the adaptor 106. In such examples, the adaptor 106 routes the second signal through a second mating connection pad 110 associated with the second transducing element 114. The process is repeated for each transducing element 114. Once the capacitance monitor 108 determines and stores a capacitance for each transducing element 114 of the transducer 112, the initialization ends. In some examples, the capacitance monitor 108 compares the initial capacitance to a threshold or acceptable range to alert the user (e.g., via the display 109) and/or another system to the state (e.g., broken, operational, indeterminate, etc.) of transducing element 114, as further described below.

Once initialized, the capacitance monitor 108 determines which of the plurality of transducing elements 114 have been damaged and/or fixed based on changes from the initial capacitance and/or an acceptable range of capacitance values. Additionally, the capacitance monitor 108 may determine a type and/or amount of damage for each transducing element 114. For example, a low capacitance (e.g., 50% below a minimum acceptable capacitance) may indicate that a wire connected to the transducing element 114 is broken around the transducer head; a very low capacitance (e.g., around 0%) may indicate that the wire connected to the transducing element 114 is broken near the connection pads 110; and a high capacitance (e.g., higher than a maximum acceptable capacitance) may indicate that there is a short in the transducing element 114. The capacitance monitor 108 continuously monitors the capacitance to each of the transducing elements 114 to determine a change from the initial measurements. The capacitance monitor 108 generates an alert (e.g., via the display 109) to alert a user (e.g., technician) and/or another system and/or corrective system if a change in capacitance occurs for any of the transducing elements 114 in the transducer 112. Thus, the user and/or another system receives real-time capacitance measurements while the acoustic probe 102 is under repair so that the user is aware of any fix and/or damage they have made without needing to wait until their repair work is complete.

Figure 2:
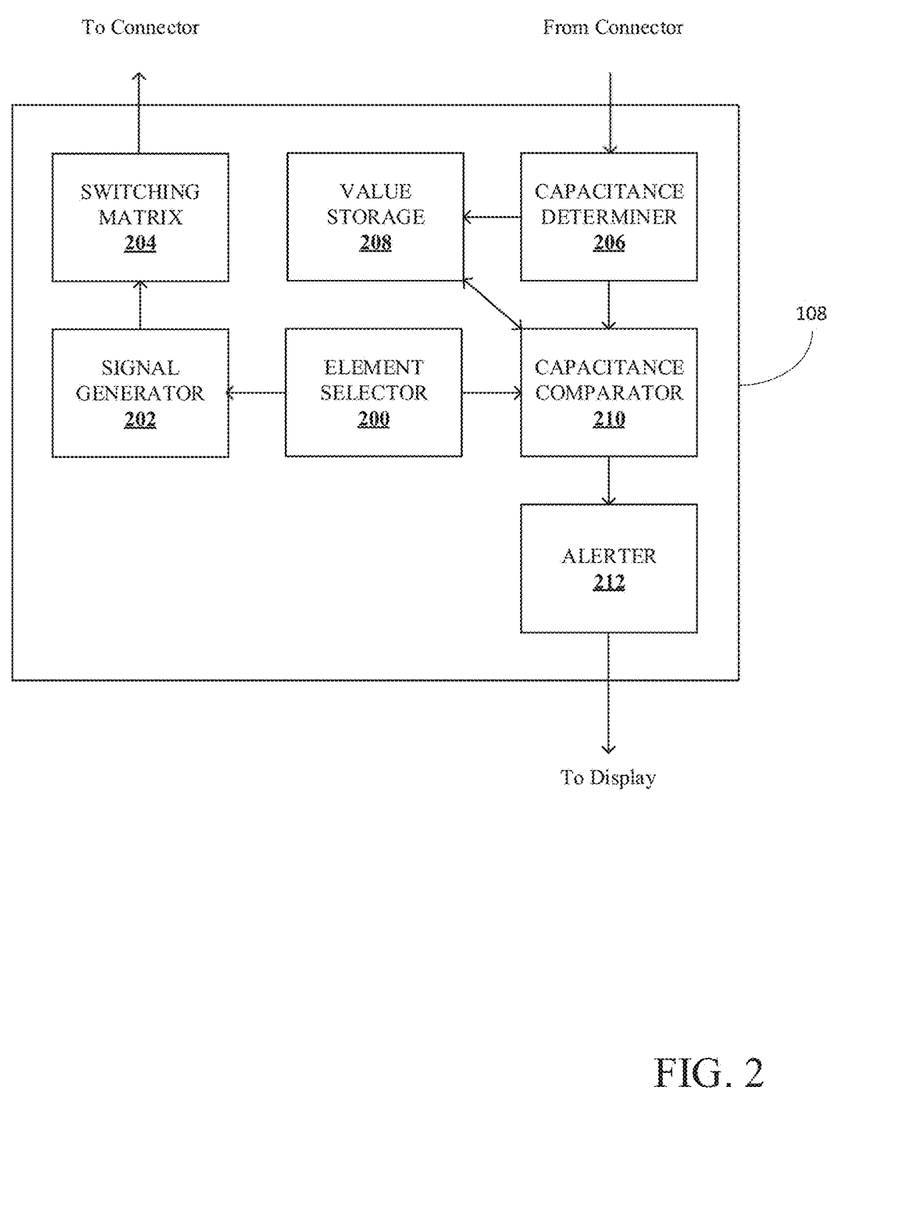
FIG. 2 is an example block diagram of a capacitance monitor of FIG. 1.

FIG. 2 is an example diagram of the capacitance monitor 108 of FIG. 1. The capacitance monitor 108 includes an element selector 200, a signal generator 202, a switching matrix 204, a capacitance determiner 206, value storage 208, a capacitance comparator 210, and an alerter 212. The element selector 200 selects a transducing element 114 whose capacitance is to be measured. The alerter 212 alerts the user and/or another system (e.g., via the display 109) if there is a change in the capacitance associated with the transducing element 114.

The element selector 200 selects a transducing element 114 from the plurality of transducing elements 114 of the transducer 112. Once selected, the element selector 200 instructs the signal generator 202 to generate a signal to measure the capacitance of the selected transducing element 114. The element selector 200 selects a new transducing element 114 to measure after the element selector 200 receives a signal from the capacitance determiner 206 that the capacitance of the previous element has been received. In some examples, the element selector 200 may weight a subset of transducing elements 114 that may be more prone to damage. In such examples, the element selector 200 may determine the capacitance of each of the subset of transducing elements 114 more often during real-time monitoring.

Once the element selector 200 selects a transducing element 114 to measure, the signal generator 202 generates a signal to be sent to the transducing element 114 in the example probe 102. In some examples, the signal is a broadband pulse that excites the transducing element 114 in the transducer 112 of the probe 102. For example, the signal may include a voltage pulse. In some examples, the digital voltage pulse signal is converted to an analog signal (e.g., by a digital-to-analog converter). In some examples, the generated signal is a waveform having a variation in voltage over time (e.g., a saw-tooth wave, a triangle wave, a square wave, etc.).

The signal generated by the signal generator 202 is routed to a selected one or more transducing elements by the switching matrix 204. The switching matrix 204 includes a bidirectional switching array to establish the desired connections. Accordingly, an array of miniature relays may be preferred in some embodiments over semiconductor-based switching integrated circuitry to limit capacitive and resistive loads. The relays may be arranged in groups to limit the number of mating connection pads 104 that may be active at any given time. Additionally, a regular circuit topology may be used to keep the electrical load substantially constant. In some examples, a correction factor determined uniquely for each element may be used to further reduce measurement errors that may be associated with electrical loading associated with the switching matrix. For example, a circuit of the monitoring device 100, once physically built, may be measured and the results mathematically removed to obtain a true measurement of each transducing element 114. The switching matrix 204 performs a mapping from one channel that corresponds to the signal generator 202 to a plurality of channels that are in communication with the adapter 106, as further described with respect to FIG. 3.

Once the electric signal is sent to the transducing element 114 of the transducer 112, the capacitance determiner 206 determines the capacitance for the transducing element 114 based on receiving a signal from the transducing element 114. In some examples, the capacitance of the transducing element 114 is determined based on a duration of time it takes to charge the transducing element 114. For example, the switching matrix may have some source resistance. In such examples, the signal generated by the signal generator 202 is transmitted through the switching matrix 204 to the transmitting elements 114 of the acoustic probe 102. As previously described, the waveform of the generated signal may have variation in voltage (e.g., ΔV) over time (e.g., Δt). In such examples, the capacitance is defined by $$C = \frac{i}{\left(\frac{\Delta V}{\Delta t}\right)}.$$

A suitable value for the source resistance in a particular embodiment may approximately 10 kΩ. While the invention is not limited to a specific shape for the capacitance-defining waveform, it may conveniently take the form of a linear ramp function, thereby providing a constant capacitance. For example, the voltage increase of the waveform could be ΔV=4.096 V over a time period of Δt=409.6 μs, thereby providing a capacitance of $C=i/10^4$ farads (F). The capacitance of each of the transducing elements 114 may be determined by generating the signal and measuring the resulting current i (e.g., via a sensor).

Alternatively, the capacitance determiner 206 may include additional circuitry (e.g., switches, comparators, counters, clocks, etc.) may be added to trigger a signal when the transducing element 114 is fully charged. In such examples, the capacitance is determined based on a duration of time between sending the generated signal and receiving the trigger. For example, a comparator and a counter may be used to determine when the voltage on the lead has reached a certain level (e.g., about 2.5 volts, representing a full charge of the transducing element 114). In such examples, a test node may be coupled to a non-inverting input of the comparator for comparison with a reference signal. The reference signal may be generated by using a voltage divider coupled to a voltage source of about 5 volts, for example. The reference signal is input into the inverting input of the comparator. In such examples, when the voltage of the lead rises to about 2.5 volts, the output of the comparator is driven high. The capacitance determiner 206 senses the output of the comparator. Once the signal from the signal generator 202 is transmitted to the transducing element 114, the capacitance determiner 206 may initiate the counter. When the capacitance determiner 206 detects that the comparator has been "tripped" (e.g., change from a digital value of '0' to a digital value of '1'), the capacitance determiner 206 stops the counter. The count from the counter can then be used by the capacitance determiner 206 to determine the capacitance of a transducing element 114 of the acoustic probe 102 using known relationships between capacitance, resistance, and charge times. For example, the change in time required to charge a capacitor to roughly 63 percent of full of its initial voltage may be referred to as a time constant r, which is directly proportional to the resistance and capacitance of a circuit. In some examples, a capacitance is fully charged after 5 time constants, or 5·τ. Thus, the capacitance determiner 206 may determine the capacitance of the transducing element 114 as follows: C=5·τ·R.

In some examples, additional circuitry (e.g., capacitance sensors) may be used to determine the capacitance and the capacitance determiner 206 may receive the capacitance value directly from the additional circuitry. During initialization, the capacitance determiner 206 transmits the acquired and/or determined capacitance value to the value storage 208. After initialization (e.g., during real-time monitoring), the capacitance determiner 206 transmits the acquired and/or determined capacitance value to the capacitance comparator 210.

The value storage 208 stores the initial capacitance for each transducing element 114. During initialization, the value storage 208 receives a measured transducing element 114 identifier (e.g., which transducing element 114 is being monitored) from the element selector 200 and the measured capacitance for the measured transducing element 114 from the capacitance determiner 206. In some examples, the value storage 208 stores the initial measured capacitance for the plurality of transducing elements 114. In some examples, the value storage 208 stores a variable representative of the capacitance. For example, the value storage 208 may store a '0' for each transducing element 114 whose capacitance is within an acceptable range of capacitance, a '1' for each transducing element 114 whose capacitance is above the acceptable range, a '2' for each transducing element 114 whose capacitance is below the acceptable range but not 0 picofarads (pF), and a '3' for each transducing element 114 whose capacitance is 0 pF. Using the variable representation, small changes in capacitance can be ignored.

The capacitance comparator 210 evaluates the measured capacitances from each transducing element 114 and determines whether the capacitance is representative with an operational transducing element 114. As previously described, the determination may be based on whether the measured capacitance is within an acceptable range. Alternatively, the determination may be based on a threshold maximum, minimum, and/or average value. After initialization (e.g., during real-time monitoring), the capacitance comparator 210 receives a measured capacitance from a transducing element 114 selected by the element selector 200. Once the measured capacitance is received by the capacitance comparator 210, the capacitance comparator 210 obtains the initial capacitance from the value storage 208. If the measured capacitance is different from the initial capacitance, the capacitance comparator 210 determines if the measured capacitance is within an acceptable range for the transducing element 114. The capacitance comparator 210 may send a signal to the alerter 212 to alert the user and/or another system based on a change in the initial capacitance. For example, if the initial capacitance of a transducing element 114 is 500 pF and the acceptable range for the transducing element 114 is between 300 pF and 700 pF, then the transducing element 114 is within the acceptable range. If, during real-time monitoring, the measured capacitance is 0 pF, the capacitance comparator 210 determines that the measured capacitance is outside the acceptable range (e.g., 300 pF to 700 pF) indicating that the user may have damaged hardware associated with the transducing element 114. Alternatively, if the initial capacitance of the transducing element 114 is 0 pF (e.g., indicating that the transducing element 114 was initially damaged) and, therefore, outside the acceptable range (e.g. 300 pF to 700 pF) and the measured capacitance of the transducing element 114 is within the acceptable range (e.g., 500 pF), the capacitance comparator 210 determines that the user has fixed hardware associated with the transducing element 114. The acceptable range may be based on user settings, manufacture settings, and/or characteristics of the acoustic probe 102. In some examples, the capacitance comparator 210 may ignore minor changes in capacitance (e.g., when an initial capacitance for the transducing element 114 is different from the measured capacitance but both capacitance values are within the acceptable range).

In some examples, the capacitance comparator 210 may aggregate the transducing elements 114 into subgroups and/or zones. In such examples, the capacitance can determine more complex acceptance patterns. The capacitance comparator 210 may send a signal to the alerter 212 based on various acceptance patterns set by a user and/or manufacture of the acoustic probe 102 and/or the monitoring device 100. For example, an example acceptance pattern may include a not trigger an alert if three transducing elements 114 are outside the acceptable range on either edge of a zone but not more than five transducing elements 114 outside the acceptable range on both edges of the zone combined. Additionally, the acceptance patterns may be different for each zone. For example, the capacitance comparator 210 may send a signal to alerter 212 if there are more than N number of failures in a first zone of the transducing elements 114, there are more than M number of failures in a second zone of the transducing elements 114, and/or there are any number of failures in a third zone of the transducing elements 114. Alternatively, any type of acceptance pattern may be used. Additionally or alternatively, the capacitance comparator 210 may send different signals to the alerter 212 based on different failures in different zones.

The alerter 212 sends an alert to the display 109 when the user has fixed and/or damaged the transducer 112. In some examples, the alert created by the alerter 212 is different based on circumstances surrounding the triggering of the alert. For example, the alerter 212 may alert the user and/or another system with a first message indicating which transducing element 114 was damaged, when hardware associated with the transducing element 114 has been damaged. Additionally, the alerter 212 may alert the user and/or another system with a second message indicating which transducing element 114 was fixed, when hardware associated with the transducing element 114 has been fixed. Additionally, the alerter 212 may also indicate how the transducing element 114 was damaged based on the measured capacitance. For example, if the capacitance of the transducing element 114 increased from 500 pF (e.g., within an acceptable range) to 1000 pF (e.g., above a maximum capacitance of the acceptable range), the alerter 212 may trigger an alert identifying a short in a circuit associated with the transducing element 114.

Figure 3:
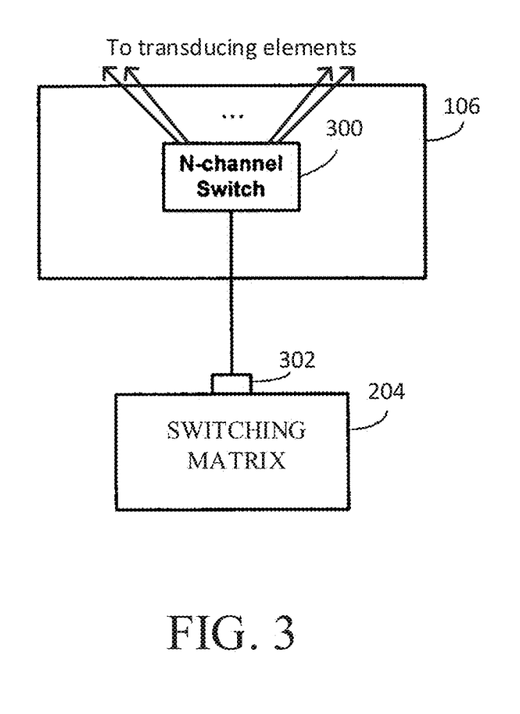
FIG. 3 is an example communication between a switching matrix and an adapter of FIG. 1.

FIG. 3 is an example of illustration of the switching matrix 204 of FIG. 2 in communication with the adapter 106 of FIG. 1. The example illustration includes the adapter 106, the relate matrix 204, an N-channel switch 300, and a connector 302. The switching matrix 204 transmits an electric and/or acoustic signal to a transducing element 114 through the connector 302 and the N-channel switch 300 of the adapter 106.

In the illustrated example of FIG. 3, the monitoring device 100 may be used to test a 192-channel probe or system. In some examples, interfacing the 192 channels through the adapter 106 with the switching matrix 204 may be accomplished with, for example, a 260-pin zero-insertion force ("ZIF") connector 302. Such connectors 302 are readily available commercially at reasonable cost and have sufficient numbers of pins to accommodate the 192 channels as well as power connections, ground connections, computer connections, etc. However, if the testing apparatus is also to be used to test a 256-channel probe or system, the capacity of the connector 302 may be insufficient. Replacement of the 260-pin ZIF connector 302 with a larger connector greatly increases the overall cost of the monitoring device 100 and makes inventory control difficult because such larger connectors are considerably more costly and have poor distribution availability.

These disadvantages are avoided by including the N-channel switch 300 in the adapter 106. Referring again to the example above, a 256-channel probe or system may be tested with the monitoring device 100 even with a 260-pin ZIF connector 302 since some of the mapping of channels may be performed by a 64-channel switch 300. In the case of a probe test, the channel may be selected by a combination of routing through the switching matrix 204 and the N-channel switch 300. In the case of a system test, use of the natural system cycling may similarly be accommodated by a combination of routing through the switching matrix 204 and the N-channel switch 300.

Figure 4A:
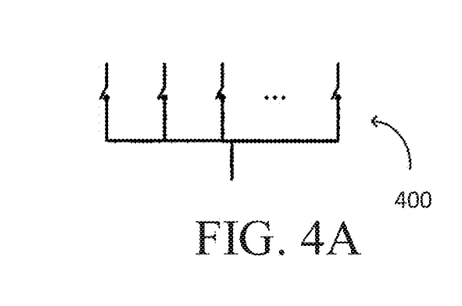
FIG. 4A is an example circuit of an N-channel switch of FIG. 3.
Figure 4B:
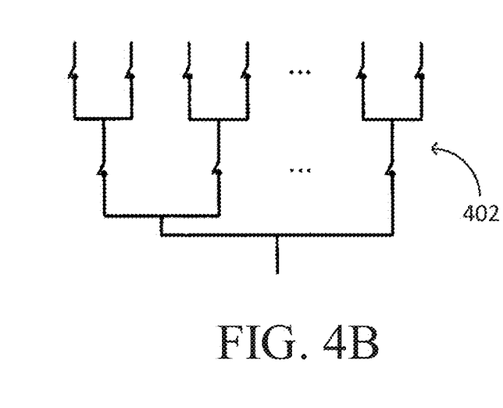
FIG. 4B is an alternative example circuit of the N-channel switch of FIG. 3.

FIGS. 4A and 4B show two different example configurations for the N-channel switch 300 of FIG. 3. For example, FIG. 4A illustrates an embodiment in which a plurality N of single-channel switches that are used directly to implement the N-channel switch 300, with one terminal of each of the single-channel switches being connected together electrically. Alternatively, FIG. 4B illustrates single-channel switches that are electrically connected in a tree arrangement to form the N-channel switch 402. The tree arrangement defines banks of single-channel switches such that at any time no more than one bank is active. For example, banks may be provided that have only sixteen, eight, or some other appropriate number of single-channel switches. Although the total number of single-channel switches in such an embodiment may be greater than N, this configuration limits the capacitance associated with the adapter 106, which might otherwise interfere with the capability of the testing apparatus to make accurate measurements. The tree arrangement is, thus, particularly useful in embodiments where capacitance determinations are used as part of the acoustic probe or system diagnosis.

Figure 5:
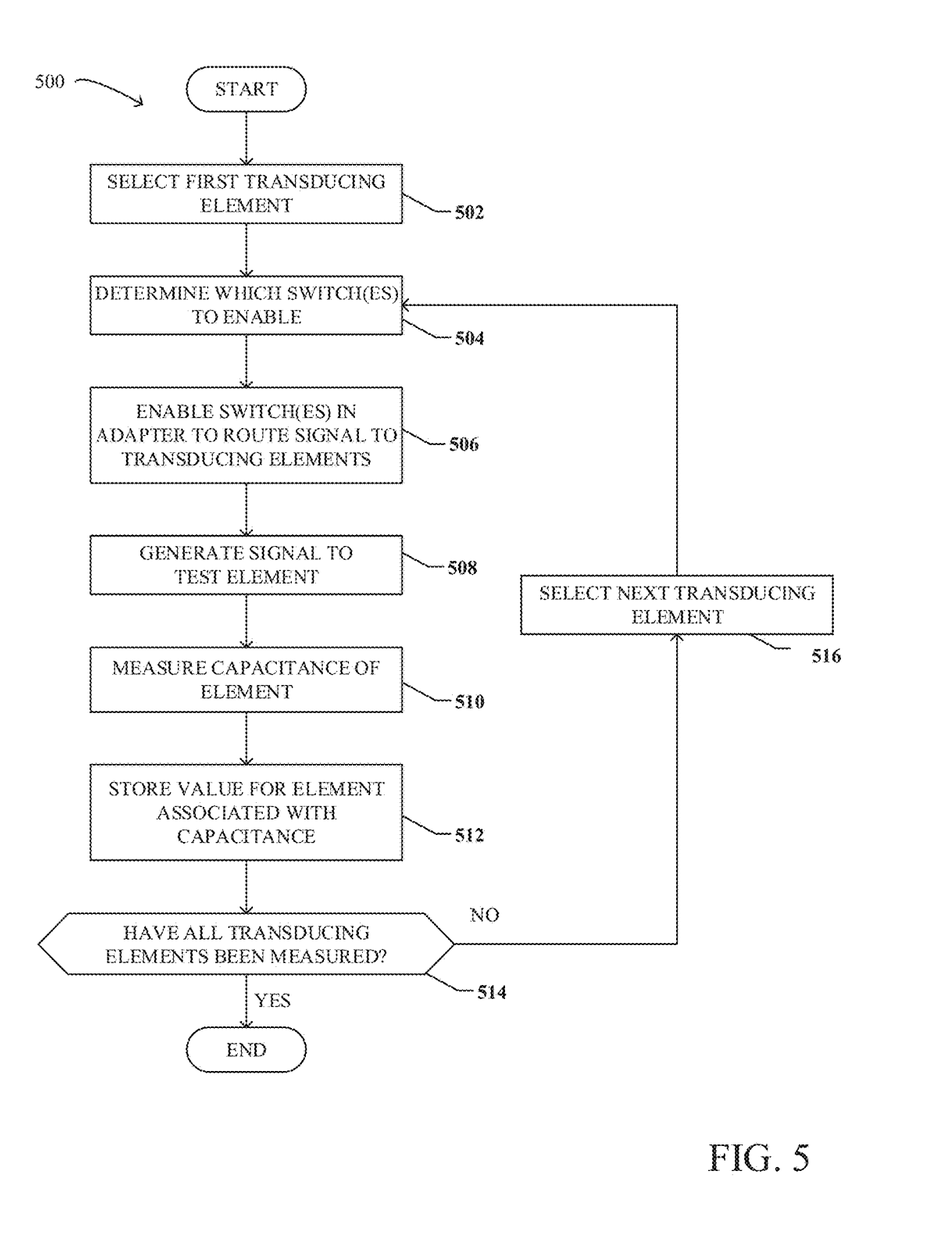
FIGS. 5 and 6 are flowcharts representative of example machine readable instructions that may be executed to implement the capacitance controller of FIG. 2 to monitor capacitances of transducing elements of FIG. 1.
Figure 6:
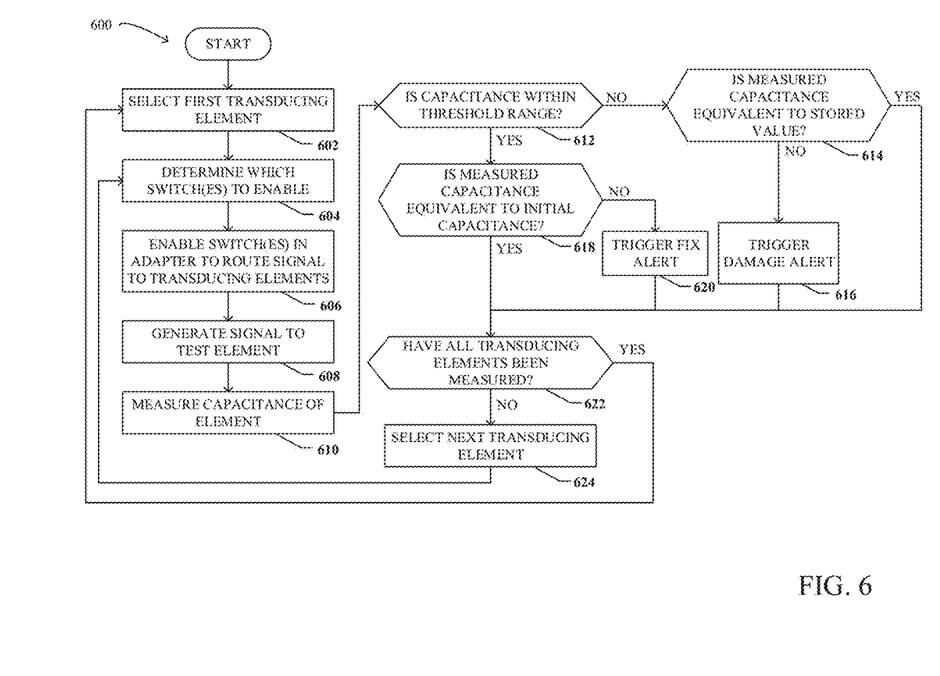

While example implementations of the capacitance monitor 108 of FIG. 1 are illustrated in FIG. 2, elements, processes and/or devices illustrated in FIGS. 5-6 may be combined, divided, re-arranged, omitted, eliminated and/or implemented in any other way. Further, the example element selector 200, the example signal generator 202, the example switching matrix 204, the example capacitance determiner 206, the example value storage 208, the example capacitance comparator 210, the example alerter 212, and/or, more generally, the capacitance monitor 108 of FIG. 2 may be implemented by hardware, machine readable instructions, software, firmware and/or any combination of hardware, machine readable instructions, software and/or firmware. Thus, for example, any of the example element selector 200, the example signal generator 202, the example switching matrix 204, the example capacitance determiner 206, the example value storage 208, the example capacitance comparator 210, the example alerter 212, and/or, more generally, the capacitance monitor 108 of FIG. 2 can be implemented by analog and/or digital circuit(s), logic circuit(s), programmable processor(s), application specific integrated circuit(s)

(ASIC(s)), programmable logic device(s) (PLD(s)) and/or field programmable logic device(s) (FPLD(s)). When reading any of the apparatus or system claims of this patent to cover a purely software and/or firmware implementation, at least one of the example element selector 200, the example signal generator 202, the example switching matrix 204, the example capacitance determiner 206, the example value storage 208, the example capacitance comparator 210, the example alerter 212, and/or, more generally, the capacitance monitor 108 of FIG. 2 is/are hereby expressly defined to include a tangible computer readable storage device or storage disk such as a memory, a digital versatile disk (DVD), a compact disk (CD), a Blu-ray disk, etc. storing the software and/or firmware. Further still, the example capacitance monitor 108 of FIG. 2 includes elements, processes and/or devices in addition to, or instead of, those illustrated in FIGS. 5 and 6, and/or may include more than one of any or all of the illustrated elements, processes and devices.

Flowcharts representative of example machine readable instructions for implementing the capacitance monitor of FIG. 2 are shown in FIGS. 5 and 6. In the examples, the machine readable instructions comprise a program for execution by a processor such as the processor 812 shown in the example processor platform 800 discussed below in connection with FIG. 8. The program may be embodied in machine readable instructions stored on a tangible computer readable storage medium such as a CD-ROM, a floppy disk, a hard drive, a digital versatile disk (DVD), a Blu-ray disk, or a memory associated with the processor 812, but the entire program and/or parts thereof could alternatively be executed by a device other than the processor 812 and/or embodied in firmware or dedicated hardware. Further, although the example program is described with reference to the flowcharts illustrated in FIGS. 5 and 6, many other methods of implementing the example capacitance monitor 108 of FIG. 2 may alternatively be used. For example, the order of execution of the blocks may be changed, and/or some of the blocks described may be changed, eliminated, or combined.

As mentioned above, the example processes of FIGS. 5 and 6 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 5 and 6 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The example machine readable instructions illustrated in FIG. 5 may be executed to cause the capacitance monitor 108 of FIG. 2 to determine the initial capacitance values of the transducing elements 114 of FIG. 1. Although the example flowchart 500 of FIG. 5 depicts example steps in a given order, these steps are not exhaustive, various changes and modifications may be affected by one skilled in the art within the spirit and scope of the disclosure. For example, blocks illustrated in the flowchart 500 may be performed in an alternative order or may be performed in parallel.

FIG. 5 is an example flowchart 500 representative of example machine readable instructions that may be executed to cause the capacitance monitor 108 of FIG. 2 to determine the initial capacitance values of the transducing elements 114 of FIG. 1. The initial capacitance values for each transducing elements 114 will be compared to capacitance measurements from each of the transducing elements 114 during a real-time monitoring process to trigger an alert based on an identified change.

At block 502, the element selector 200 selects a first transducing element 114 from the plurality of transducing elements 114. In some examples, the element selector may select a first transducing element 114 based transducing elements that are more likely to be damaged (e.g., transducing elements 114 on the edge of the transducer 112). At block 504, the switching matrix 204 determines which mating connection pad 104 and/or connector pin is connected to, or otherwise associated with, the selected transducing element 114 and determines how to route the generated signal to the mating connection pad 104 based characteristics of the adapter 106. For example, if the adapter 106 includes a single switch per mating connection pad 104 and/or connector pin, such as the N-channel switch 400 of FIG. 4A, the switching matrix 204 determines which switch to enable and disables the other switches to allow the generated signal to reach the first transducing element 114. Alternatively, if the adapter 106 includes a tree style switching structure, such as the N-channel switch 402 of FIG. 4B, the switching matrix 204 determines switch set of switches need to be enabled and/or disabled in order for the route the generated signal to the first transducing element 114.

At block 506, the switch(es) in the adapter 104 are enabled to allow the signal to be sent to the first transducing element 114 through the connection between the connection pads 110 and/or connector pins and the mating connection pads 104. The signal generator 202 generates a signal to test the first transducing element 114 by operating an oscillator (block 508). In some examples, the generated signal is a waveform having a variation in voltage over time (e.g., a saw-tooth wave, a triangle wave, a square wave, etc.). At block 510, a reply signal is received by the capacitance determiner 206, and the capacitance determiner 206 measures the capacitance of the first transducing element 114. As previously described, the capacitance determiner 206 may measure and/or determine the capacitance based on the amount of time it takes for the transducing element 114 to charge to a particular voltage level. Once the capacitance has been measured, the value storage 208 stores a transducing element 114 identifier and a value associated with the capacitance for the transducing element 114 (block 512). As previously described, the value may be the actual capacitance of the transducing element 114. Alternatively, the value may be a variable representative of the capacitance (e.g., '0' for capacitance within acceptable range, '1' for capacitance above the acceptable range, etc.).

At block 514, the element selector 200 determines if all the transducing elements 114 in the transducer 112 have been measured (e.g., an initial capacitance for each transducing element 114 has been measured). If the element selector 200 has not measured the capacitance for all of the transducing elements 114, the element selector selects a second transducing element 114 to measure (block 516), and the process repeats based on the new transducing element 114. If the element selector 200 has measured the capacitance for all transducing elements 114, the initialization process is complete and the capacitance monitor 108 enters into a real-time monitoring process as further described in FIG. 6. Additionally, the alerter 212 may trigger an alert to a user and/or another system, via the display 109, to the initial values of the transducing elements 114. As previously described, the alert may be a visual, audio, mechanical, and/or any other type of alert.

The example machine readable instructions illustrated in FIG. 6 may be executed to cause the capacitance monitor 108 of FIG. 2 to provide real-time triggers an alert based on measured capacitances in conjunction with FIG. 1. Although the example flowchart 600 of FIG. 6 depicts example actions in a given order, these elements are not exhaustive and, various changes and modifications may be affected by one skilled in the art within the spirit and scope of the disclosure. For example, blocks illustrated in the flowchart 600 may be performed in an alternative order or may be performed in parallel.

FIG. 6 is an example flowchart 600 representative of example machine readable instructions that may be executed to cause the capacitance monitor 108 of FIG. 2 to monitor the capacitances of the transducing elements 114 of FIG. 1 in real time. Since a user may damage all or part of a transducer 112 during repair of the acoustic probe 102, the capacitance monitor 108 monitors the capacitance of each transducing element 114 of the transducer 112 to trigger an alert identifying damage while the user repairs the acoustic probe 102.

At block 602, the element selector 200 selects a first transducing element 114 from the plurality of transducing elements 114. In some examples, the element selector may select a first transducing element 114 based transducing elements that are more likely to be damaged (e.g., transducing elements 114 on the edge of the transducer 112). At block 604, the switching matrix 204 determines which mating connection pad 104 is connected to, or otherwise associated with, the selected transducing element 114 and determines how to route the generated signal to the mating connection pad 104 based characteristics of the adapter 106. For example, if the adapter 106 includes a single switch per mating connection pad 104, such as the N-channel switch 400 of FIG. 4A, the switching matrix 204 determines which switch to enable and disables the other switches to allow the generated signal to reach the first transducing element 114. Alternatively, if the adapter 106 includes a tree style switching structure, such as the N-channel switch 402 of FIG. 4B, the switching matrix 204 determines switch set of switches need to be enabled and/or disabled in order for the route the generated signal to the first transducing element 114.

At block 606, the switch(es) in the adapter 104 are enabled to allow the signal to be sent to the first transducing element 114 through the connection between the connection pads 110 and the mating connection pads 104. The signal generator 202 generates a signal to test the first transducing element 114 (block 608). At block 610, a reply signal is received by the capacitance determiner 206 and the capacitance determiner 206 measures the capacitance of the first transducing element 114. As previously described, the capacitance determiner 206 may measure and/or determine the capacitance based on the amount of time it takes for the transducing element 114 to charge to a voltage level. For example, the capacitance of the transducing element 114 may be determined based on a duration of time it takes to charge the transducing element 114.

Figure 7:
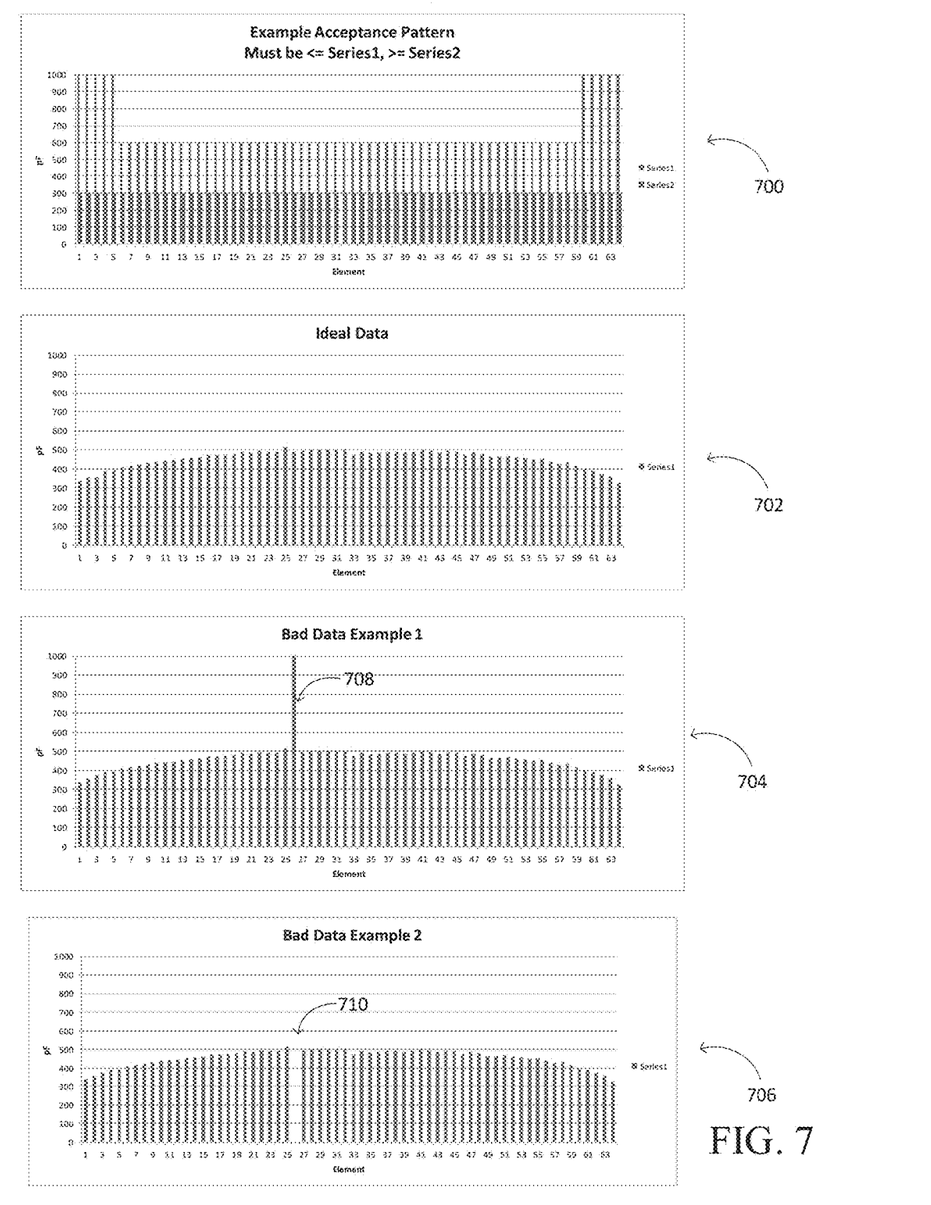
FIG. 7 is an illustration of example graphs displaying example capacitance measured by the capacitance monitor of FIG. 1.

At block 612, the capacitance comparator 210 determines if the measured capacitance is within an acceptable range appropriate for the transducing element 114. As previously described, the acceptable range may be preset and/or customized based on user settings, manufacture settings, and/or characteristics of the acoustic probe 102. Additionally, each of the transducing elements 114 may have a different acceptable range of acceptable capacitances. If the capacitance comparator 210 determines that the capacitance for the transducing element 114 is not within the acceptable range, the capacitance comparator 210 obtains the initial value of the capacitance stored in the value storage 208 during initialization. The acceptable is range of capacitance values are associated with operational transducing elements 114, as further described with respect to FIG. 7A. The acceptable range may be based on user settings, manufacture settings, and/or characteristics of the acoustic probe 102, for example. At block 614, the capacitance comparator 210 determines if the measured capacitance is equivalent (e.g., equal or virtually equal) to the stored initial value for the transducing element 114. If the measured capacitance is equivalent to the stored initial value for the transducing element 114, an alert is not triggered, since the initialization has already determined that the transducing element 114 is damaged. For example, if the initialization determines that the tenth transducing element 114 is damaged, it may be inconvenient or distracting to continue to trigger an alert identifying that the damaged transducing element 114 is still damaged. If the measured capacitance is not equivalent to the stored initial value, the alerter 212 may trigger the display 109 to trigger an alert identifying a problem (e.g., damage) (block 616). For example, if a cable and/or wire associated with a transducing element 114 is damaged (e.g. a brake in the cable and/or wire) or a short is created, the alerter 212 will trigger an alert via the display 109. In some examples, the alerter 212 may trigger an alert identifying which transducing element 114 and/or how the transducing element 114 was damaged (e.g., based on the measured capacitance). For example, if the capacitance increased to a capacitance above the acceptable range, the alerter 212 may trigger an alert identifying a short was created at the transducing element 114 and/or hardware (e.g., wire, cable, etc.) associated with the transducing element 114. Alternatively, if the capacitance decreased to a capacitance below the acceptable range, the alerter 212 may trigger an alert identifying that the cable and/or wire was broken (e.g., creating an open circuit). Additionally, the alerter 212 may customize the alert based on the capacitance. In some examples, the capacitance comparator 210 updates the initial stored value based on the new measured value. In such examples, the initial value is updated to prevent repeating damage alerts for future capacitance measurements. In some examples, the capacitance comparator 210 ignores slight changes (e.g., within a standard deviation and/or other tolerance, etc.) in capacitance.

Returning to block 612, if the capacitance is within the acceptable range for the transducing element 114, the capacitance comparator 210 determines if the measured capacitance is equivalent to initial capacitance (block 618). If the measured capacitance is equivalent to the stored initial capacitance, an alert is not triggered. If the measured capacitance is not equivalent to the stored initial capacitance for the transducing element 114, the alerter 212 triggers an alerter, via the display 109, that the transducing element 114 has been fixed (block 620). For example, a transducing element 114 that is within the acceptable range but previously was not within the acceptable range is indicative that the transducing element 114 has been fixed. In some examples, the capacitance comparator 210 updates the initial stored value based on the new measured value. In such examples, the initial value is updated to prevent repeating fix alerts for future capacitance measurements.

After the capacitance comparator 210 has determined whether or not to trigger an alert based on the capacitance, the element selector 200 determines if the capacitances have been measure for all transducing elements 114 (block 622). If the element selector 200 has determined that the capacitances have been measured for all transducing elements 114, the element selector 200 restarts the process. In some examples, the element selector 200 may repeat measurements for a subset of transducing elements 114 that are more susceptible to damage before restarting the process. In some examples, the element selector 200 may track which transducing elements 114 have been measured based on a count. In such examples, the element selector 200 may additionally reset the count before the measurements are restarted. If the capacitances have not all been measured for the transducing elements 114, the element selector 200 selects a new unmeasured transducing element 114 to measure (block 624). In some examples, the capacitance for an already measured transducing element 114 may be measured again (e.g., for the subset of transducing element 114 that are more susceptible to damage). Once the element selector 200 selects the new unmeasured transducing element 114, the process is repeated to determine whether or not to trigger an alert based on a potential change in capacitance for the next transducing element 114.

FIG. 7 illustrates example graphs 700, 702, 704, 706 displaying sample capacitance data used to trigger alerts. FIG. 7 includes an acceptable range graph 700, an ideal data graph 702, a first bad example graph 704, and a second example of bad data graph 706.

The acceptable range graph 700 displays example acceptable ranges for each of the transducing elements 114 in the transducer 112. In the illustrated acceptable range graph 700, transducing elements '1' through '5' and '60' through '64' have an acceptable range from 300 pF to 1000 pF, whereas transducing elements '6' through '59' have an acceptable range from 300 pF to 600 pF. As previously described, the acceptable range may be different for each of the transducing elements 114 and may be preset and/or customizable based on user settings, manufacture settings, and/or characteristics of the acoustic probe 102. In some examples, the transducing elements 114 may be grouped (e.g., aggregated) into subgroups (e.g., zones) of transducing elements 114. In such examples, each subgroup of transducing elements 114 may have different acceptable ranges.

The ideal data graph 702 displays example ideal capacitance values from the 64 transducing elements 114 of the transducer 112. As illustrated by the ideal data graph 702, all the 64 transducing elements 114 have capacitance within the acceptable ranges of the acceptable range graph 700. For example, the $26^{th}$ transducing element has a capacitance of roughly 500 pF; and as described above, the acceptable range for the $26^{th}$ transducing element is from 300 pF to 600 pF. Thus, the $26^{th}$ transducing element is within the associated acceptable range.

The first bad example graph 704 displays measured capacitances from example transducer 112 with a damaged transducing element. As illustrated by the first bad example graph 704, the capacitance of the $26^{th}$ transducing element 708 is roughly 1000 pF which is well outside the acceptable range (e.g., between 300 pF and 600 pF). As previously described, a high capacitance may signify a short associated with the $26^{th}$ transducing element 708.

The second bad example graph 706 displays measured capacitance from the example transducer 112 with a damaged transducing element. As illustrated by the second bad example graph 706, the capacitance of the $26^{th}$ element 710 is roughly 0 pF which is well outside the acceptable range (e.g., between 300 pF and 600 pF). As previously described, a very low capacitance (e.g. nearly 0 pF) may signify that the wire connected to the transducing element is broken near the connection pads 110. In some examples, the alerter 212 may include any of the graphs 700, 702, 704, 708 to trigger an alert via the display 109.

Figure 8:
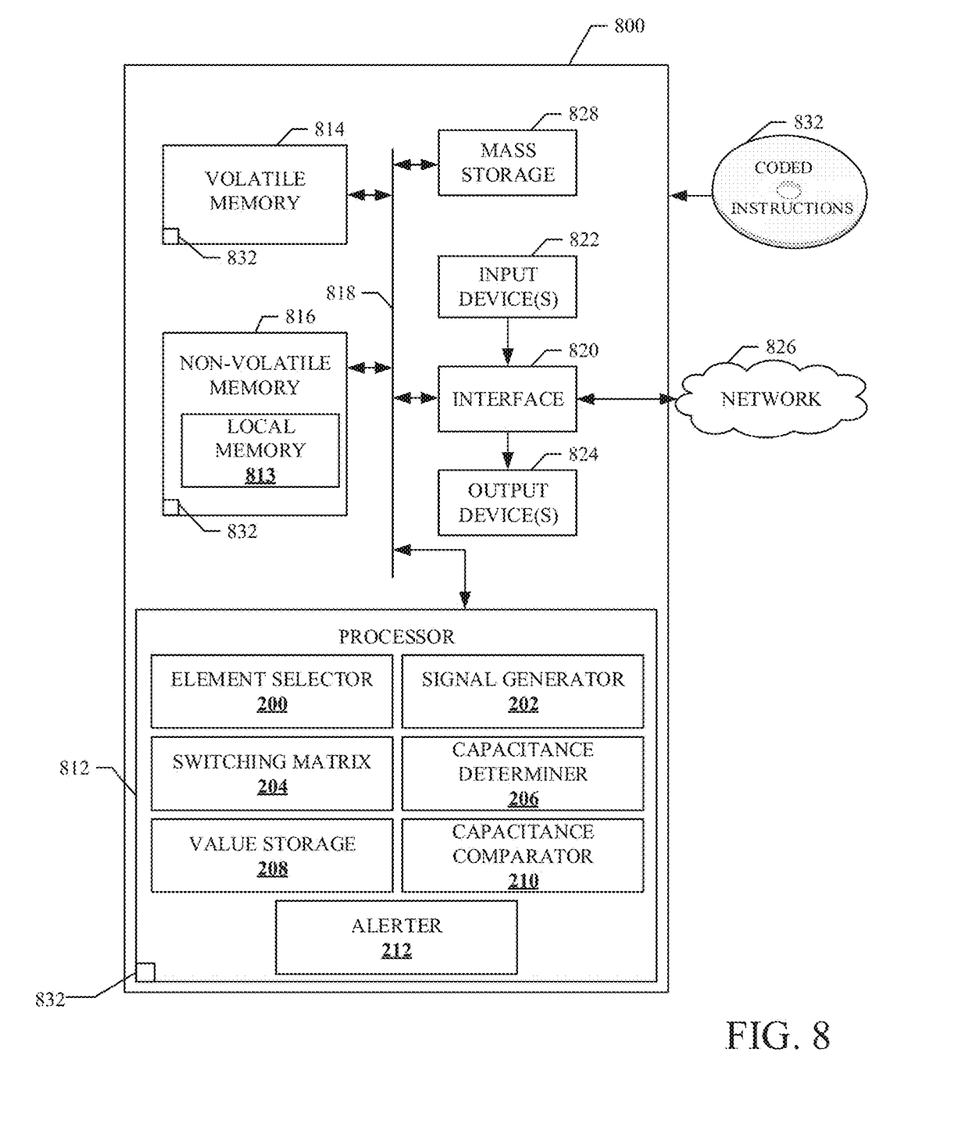
FIG. 8 is a block diagram of a processor platform structured to execute the example machine readable instructions of FIGS. 5 and 6 to control the capacitance monitor of FIG. 1.

FIG. 8 is a block diagram of an example processor platform 800 capable of executing the instructions of FIG. 8 to implement the capacitance monitor 108 of FIGS. 1 and 2. The processor platform 800 can be, for example, a server, a personal computer, a mobile device (e.g., a cell phone, a smart phone, a tablet such as an iPad™), a personal digital assistant (PDA), an Internet appliance, or any other type of computing device.

The processor platform 800 of the illustrated example includes a processor 812. The processor 812 of the illustrated example is hardware. For example, the processor 812 can be implemented by integrated circuits, logic circuits, microprocessors or controllers from any desired family or manufacturer.

The processor 812 of the illustrated example includes a local memory 813 (e.g., a cache). The example processor 812 of FIG. 8 executes the instructions of FIGS. 5 and 6 to implement the example element selector 200, the example signal generator 202, the example switching matrix 204, the example capacitance determiner 206, the example value storage 208, the example capacitance comparator 210, the example alerter 212 of FIG. 2 to implement the example capacitance monitor 108. The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a clock controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

The coded instructions 832 of FIGS. 5 and 6 may be stored in the mass storage device 828, in the volatile memory 814, in the non-volatile memory 816, and/or on a removable tangible computer readable storage medium such as a CD or DVD.

From the foregoing, it would be appreciated that the above disclosed methods, apparatus, and articles of manufacture monitor capacitance of transducing elements in an acoustic probe in real time while the probe is under repair. In such examples, a user can be alerted to damages and/or fixes to the acoustic probe as soon as the damages and/or fixes occur. In this manner, a technician does not need to wait until his repair work is complete to determine whether or not his work was a success. Alerting the technician to damages and/or fixes in real time saves both time and money.

Conventional methods test capacitances of transducing elements in an acoustic probe after the probe has been repaired. In such examples, if a technician works on repairing a probe for an hour and, while working, damages a transducing element within the first 2 minutes, the technician would not be aware of the damage until after the work is complete. In such examples, the technician may have spent wasted time by unknowingly working on damaged hardware. Unlike conventional methods, the technician is alerter to any discrepancies in real time so that the technician can adjust repair accordingly.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A method for testing an acoustic probe having a plurality of transducing elements during repair of the acoustic probe, the method comprising:
    storing, at a first time, a value corresponding to an initial capacitance of a transducing element of the plurality of transducing elements, the initial capacitance measured during initialization of the acoustic probe for repair;
    determining, at a second time subsequent to the first time, a capacitance of the transducing element of the plurality of transducing elements;
    when the capacitance of the transducing element is (A) outside of an acceptable range and (B) different than the stored value corresponding to the initial capacitance of the transducing element, triggering an alert and continuing to determine the capacitance of the transducing element during the repair of the acoustic probe; and
    when the capacitance of the transducing element is within the acceptable range, continuing to determine the capacitance of the transducing element during the repair of the acoustic probe.

2. The method of claim 1, wherein triggering an alert includes at least one of an audio, a visual, or a mechanical alert identifying that damage to the transducing element has occurred during the testing of the acoustic probe.

3. The method of claim 1, wherein the acceptable range is representative of a range of capacitance values associated with an operational transducing element.

4. The method of claim 1, wherein the triggering of the alert includes:
    a first alert if the capacitance of the transducing element is larger than the initial capacitance of the transducing element; and
    a second alert, different than the first alert, if the capacitance of the transducing element is smaller than the initial capacitance of the transducing element.

5. The method of claim 1, further including, when the capacitance of the transducing element is (A) within the acceptable range and (B) different than the initial capacitance of the transducing element, triggering an alert that the transducing element is functional.

6. The method of claim 1, wherein the transducing element is a first transducing element, further including:
    storing, at a third time, a second value corresponding to a second initial capacitance of a second transducing element of the plurality of transducing elements, the second initial capacitance measured during the initialization of the acoustic probe for repair;
    determining, at a fourth time subsequent to the third time, a capacitance of the second transducing element of the plurality of transducing elements, the second transducing element being different than the first transducing element;
    when the capacitance of the second transducing element is (A) outside a second acceptable range and (B) different than the second stored value corresponding to the second initial capacitance of the second transducing element, triggering the alert and continuing to determine the capacitance of the second transducing element; and
    when the capacitance of the second transducing element is within the second acceptable range, continuing to determine the capacitance of the second transducing element.

7. The method of claim 6, wherein the acceptable range is different than the second acceptable range.

8. An apparatus for testing an acoustic probe having a plurality of transducing elements during repair of the acoustic probe, the apparatus comprising:
    storage to store, at a first time, a value corresponding to an initial capacitance of a transducing element of the plurality of transducing elements, the initial capacitance measured during initialization of the acoustic probe for repair;

a capacitance determiner to determine, at a second time subsequent to the first time, a capacitance of the transducing element of the plurality of transducing elements; and an alerter to, when the capacitance of the transducing element is (A) outside of an acceptable range and (B) different than the stored value corresponding to the initial capacitance of the transducing element, trigger an alert, the capacitance determiner to continue to determine the capacitance of the transducing element during the repair of the acoustic probe; and the capacitance determiner to, when the capacitance of the transducing element is within the acceptable range, continue to determine the capacitance of the transducing element during the repair of the acoustic probe.

9. The apparatus of claim 8, wherein the alert includes at least one of an audio, a visual, or a mechanical alert identifying that damage to the transducing element has occurred during the testing of the acoustic probe.

10. The apparatus of claim 8, wherein the acceptable range is representative of a range of capacitance values associated with an operational transducing element.

11. The apparatus of claim 8, wherein the alerter is further to:

trigger a first alert if the capacitance of the transducing element is larger than the initial capacitance of the transducing element; and trigger a second alert, different than the first alert, if the capacitance of the transducing element is smaller than the initial capacitance of the transducing element.

12. The apparatus of claim 8, wherein the alerter is to, when the capacitance of the transducing element is (A) within the acceptable range and (B) different than the initial capacitance of the transducing element, trigger an alert that the transducing element is functional.

13. The apparatus of claim 8, wherein:

the storage is to store, at a third time, a second value corresponding to a second initial capacitance of a second transducing element of the plurality of transducing elements, the second initial capacitance measured during the initialization of the acoustic probe for repair;

the capacitance determiner is to determine, at a fourth time subsequent to the third time, a capacitance of the second transducing element of the plurality of transducing elements, the second transducing element being different than the first transducing element;

the alerter is to, when the capacitance of the second transducing element is (A) outside a second acceptable range and (B) different than the second stored value corresponding to the second initial capacitance of the second transducing element, trigger the alert, the capacitance determiner to continue to determine the capacitance of the second transducing element during repair of an acoustic probe; and the capacitance determiner to, when the capacitance of the second transducing element is within the second acceptable range, continue to determine the capacitance of the second transducing element during the repair of the acoustic probe.

14. The apparatus of claim 13, wherein the acceptable range is different than the second acceptable range.

15. A computer readable medium comprising instructions that, when executed, cause a machine to:

store, at a first time, a value corresponding to an initial capacitance of a transducing element of the plurality of transducing elements, the initial capacitance measured during initialization of an acoustic probe for repair;

determine, at a second time subsequent to the first time, a capacitance of the transducing element of the plurality of transducing elements;

when the capacitance of the transducing element is (A) outside of an acceptable range and (B) different than the stored value corresponding to the initial capacitance of the transducing element, trigger an alert and continue to determine the capacitance of the transducing element; and when the capacitance of the transducing element is within the acceptable range, continue to determine the capacitance of the transducing element.

16. The computer readable medium of claim 15, wherein the alert includes at least one of an audio, a visual, or a mechanical alert identifying that damage to the transducing element has occurred during the testing of the acoustic probe.

17. The computer readable medium of claim 15, wherein the acceptable range is representative of a range of capacitance values associated with an operational transducing element.

18. The computer readable medium of claim 15, wherein the instructions cause the machine to:

trigger a first alert if the capacitance of the transducing element is larger than the initial capacitance of the transducing element; and trigger a second alert, different than the first alert, if the capacitance of the transducing element is smaller than the initial capacitance of the transducing element.

19. The computer readable medium of claim 15, wherein the instructions cause the machine to when the capacitance of the transducing element is (A) within the acceptable range and (B) different than the initial capacitance of the transducing element, trigger an alert that the transducing element is functional.

20. The computer readable medium of claim 15, wherein the instructions cause the machine to:

store, at a third time, a second value corresponding to a second initial capacitance of a second transducing element of the plurality of transducing elements, the second initial capacitance measured during the initialization of the acoustic probe for repair;

determine, at a fourth time subsequent the third time, a capacitance of the second transducing element of the plurality of transducing elements, the second transducing element being different than the first transducing element;

when the capacitance of the second transducing element is (A) outside a second acceptable range and (B) different than the second stored value corresponding to the second initial capacitance of the second transducing element, trigger the alert and continue to determine the capacitance of the second transducing element; and when the capacitance of the second transducing element is within the second acceptable range, continue to determine the capacitance of the second transducing element.

21. The computer readable medium of claim 20, wherein the acceptable range is different than the second acceptable range.

22. The method of claim 1, wherein, when the capacitance of the transducing element is (A) outside of an acceptable range and (B) equivalent to the stored value corresponding to the initial capacitance of the transducing element, not triggering an alert and continuing to determine the capacitance of the transducing element.

23. The apparatus of claim 8, wherein, when the capacitance of the transducing element is (A) outside of an acceptable range and (B) equivalent to the stored value corresponding to the initial capacitance of the transducing element, the alerter is to not trigger an alert and the capacitance determiner is to continue to determine the capacitance of the transducing element.

24. The computer readable medium of claim 1, wherein the instructions cause the machine to, when the capacitance of the transducing element is (A) outside of an acceptable range and (B) equivalent to the stored value corresponding to the initial capacitance of the transducing element, not trigger an alert and continue to determine the capacitance of the transducing element.

* * * * *